United States Patent [19]

Petusky

[11] Plant 4,483

[45] Nov. 13, 1979

[54] CHRYSANTHEMUM NAMED FREE SPIRIT

[75] Inventor: Kerry S. Petusky, West Chicago, Ill.

[73] Assignee: Pan-American Plant Company, West Chicago, Ill.

[21] Appl. No.: 964,436

[22] Filed: Nov. 28, 1978

[51] Int. Cl.[2] ..... A01H 5/00

[52] U.S. Cl. ..... Plt./77

[58] Field of Search ..... Plt./77

*Primary Examiner*—Robert E. Bagwill

*Attorney, Agent, or Firm*—Chas. W. Rummler

[57] ABSTRACT

A greenhouse chrysanthemum cultivar of the pot plant type originated as a sport of the variety "Spirit" and distinguished by its large, generally white blooms having quilled ray florets which project radially from an upstanding group of inner florets having a pale yellow cast.

4 Drawing Figures

BACKGROUND OF THE NEW PLANT

This new chrysanthemum was discovered by me in November 1976 in a field of the variety "Spirit" (U.S. Plant Pat. No. 3,813) being grown in greenhouse at West Chicago, Ill., in connection with breeding efforts carried on with the object of developing new and improved chrysanthemum varieties for the commercial market. Because of the novel characteristics of this sport, it was reproduced by me by means of cuttings and subsequent propagation of this new plant by vegetative cuttings has shown its novel features to hold true from generation to generation and to appear to be firmly fixed. Propagation of this new variety on a commercial scale is now being done at Cortez, Fla., and at West Chicago, Ill.

DESCRIPTION OF THE DRAWINGS

My new chrysanthemum cultivar is illustrated by the accompanying drawings, one sheet of which is a photographic view in full color made in June 1978 and showing a potted plant in full bloom, and the second sheet being a print of a machine copy of typical leaves of the new plant at several stages of maturity.

DESCRIPTION OF THE NEW PLANT

The following is a detailed description of the new chrysanthemum variety with color designations according to The R.H.S. Colour Chart published by The Royal Horticultural Society of London, England.

THE PLANT

Origin: Sport.

Parentage: "Spirit", Plant Pat. No. 3,813.

Classification:

*Botanic.*—*Chrysanthemum morifolium.*

*Commercial.*—Greenhouse pot plant.

Form: Perennial herbaceous bush.

Height: 30–34 cm.

Growth: Terminal, upright and vigorous, sturdy and with very good strength.

Branching: Normal, sturdy and strong under natural conditions.

Foliage:

*Quantity.*—Abundant with 5 to 7 leaves on about 10 cm. of stem length.

*Leaf size.*—Length — about 6.2 to 10.1 cm. Width — 2.9 to 6.5 cm.

*Leaf shape.*—Lobed, lanceolate and slightly serrated.

*Surface aspect.*—Canescent.

*Color.*—Upper side — 147A. Under side — 147B.

*Venation.*—Pinnately veined.

*Petioles.*—Length — about 1.2 to 2.2 cm.

THE BUD

Form: Globular.

Size: 1.2 to 1.5 cm. in diameter and about 0.8 to 1.1 cm. in depth.

Opening Rate: The bud opens slowly.

Color:

*When phyllaries first divide.*—145B.

*When florets begin to unfurl.*—8D.

Phyllaries: The outside of the receptacle bears many involucral bracts which are upstanding and spear-shaped.

*Color.*—Inside — 137A. Outside — 137B.

*Surface aspect.*—Pubescent.

Penduncle: Erect, very strong and about 2.0 to 2.4 cm. in length.

*Surface aspect.*—Pubescent.

THE FLOWER

Flowering capability: Recommended for year-around flowering with photoperiod control.

*Response.*—9 weeks.

*Natural flowering season.*—October 27 to November 5.

Blooms:

*Flower type.*—Composite and quilled.

*Size.*—Large. Diameter — about 12.0 to 13.5 cm. Depth — about 4.5 to 5.5 cm.

*Borne.*—Singly when disbudded and in multiples when grown as a spray plant.

*Shape.*—When bloom first opens — cup-shaped. As the bloom matures — it tends to flatten out.

*Florets.*—Numerous in number.

*Form.*—Quilled.

| | | May | June |
|---|---|---|---|
| *Color*— | Outer florets: | | |
| | Upper side - | 155D | 155D |
| | Under side - | 155D | 155D |
| | Inside florets: | | |

-continued

| | May | June |
|---|---|---|
| Upper side - | 11D and 155D | 11D and 155D |
| Reverse side - | 11D and 155D | 11D and 155D |
| Tonality at a distance of about 2 meters: Between 11D and 155D. | | |

*Firmness.*—Medium.
*Appearance.*—Very slight shine.
*Discoloration.*—None.
*Persistence.*—The florets hang on and dry.
*Peduncle.*—Sturdy and upright. Length: About 2.0 to 2.4 cm. Color: 147B.
*Fragrance.*—Typical chrysanthemum.
*Lasting quality.*—On the plant — 3 weeks. The blooms of this plant are not recommended for cut flower use.

REPRODUCTIVE ORGANS

Stamens:
*Arrangement.*—Syngenesious. Number — 5.
*Filaments.*—About 2 to 4 mm. in length.

*Color.*—Light yellow.
*Pollen.*—Color — yellow.
Pistils: Number — 1 to each ray and disc floret.
*Styles.*—4 to 6 mm. in length.
*Stigma.*—Color — yellow.
Ovaries: Inferior, bicarpellate.

This new cultivar of potted chrysanthemum, when compared to its parent, is particularly characterized by its quill-shaped ray florets which radiate from an upstanding group of inner florets and appear as though lying in a more-or-less flat plane. This new variety has a slightly taller plant habit, averaging about 4 cm. taller than its parent, and is otherwise quite similar to its parent in its general growth characteristics and form.

I claim:

1. A new and distinct cultivar of chrysanthemum pot plant, substantially as herein shown and described, particularly characterized in uniqueness, when compared with its parent "Spirit", by its quill-shaped ray florets which project in a radial fashion from an upstanding group of the inner or disc florets.

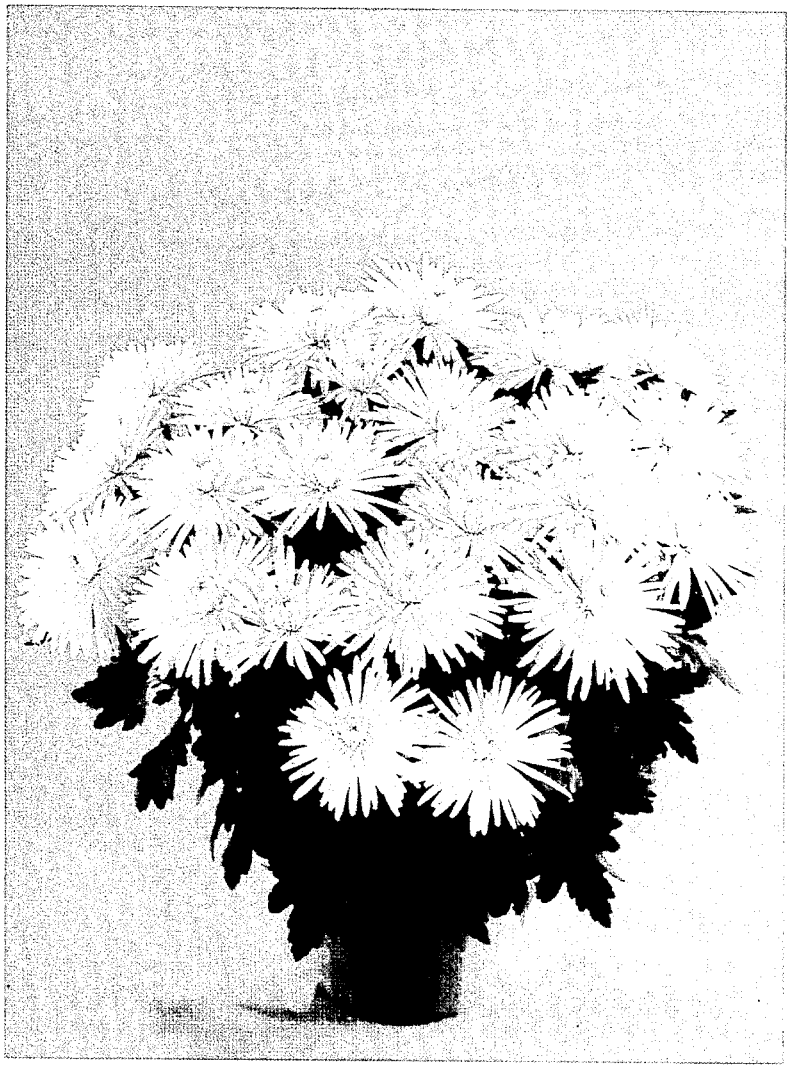

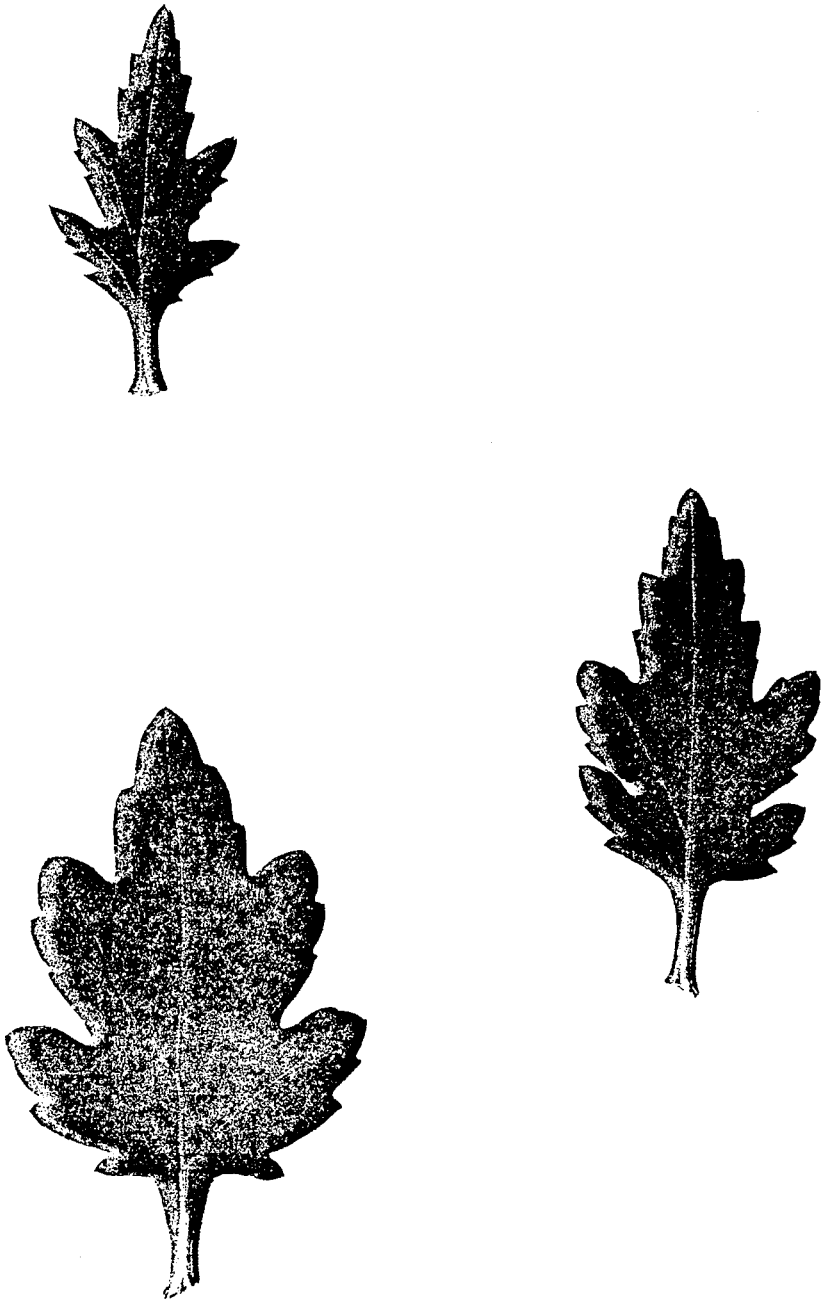

* * * * *